(12) United States Patent
Park et al.

(10) Patent No.: US 11,069,738 B2
(45) Date of Patent: Jul. 20, 2021

(54) INFRARED DETECTOR AND INFRARED SENSOR INCLUDING THE SAME

(71) Applicant: SAMSUNG ELECTRONICS CO., LTD., Suwon-si (KR)

(72) Inventors: Changyoung Park, Yongin-si (KR); Sanghun Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/384,014

(22) Filed: Apr. 15, 2019

(65) Prior Publication Data

US 2019/0245001 A1    Aug. 8, 2019

Related U.S. Application Data

(63) Continuation of application No. 15/870,022, filed on Jan. 12, 2018, now Pat. No. 10,304,896.

(30) Foreign Application Priority Data

Aug. 28, 2017  (KR) .......................... 10-2017-0108847

(51) Int. Cl.
*H01L 21/00* (2006.01)
*H01L 27/146* (2006.01)
(Continued)

(52) U.S. Cl.
CPC ........ *H01L 27/14649* (2013.01); *A61B 5/443* (2013.01); *B82Y 20/00* (2013.01); *G01J 1/44* (2013.01); *G01J 5/024* (2013.01); *G01J 5/046* (2013.01); *G01J 5/0853* (2013.01); *G01N 21/3554* (2013.01); *H01L 27/146* (2013.01); *H01L 27/14669* (2013.01); *H01L 27/14694* (2013.01); *H01L 31/022466* (2013.01);
(Continued)

(58) Field of Classification Search
CPC ..... H01L 27/14649; G01J 5/046; B82Y 20/00
See application file for complete search history.

(56) References Cited

U.S. PATENT DOCUMENTS 6,529,767 B1 *  3/2003  Woo .................... A61B 5/0075
                                                 600/473
7,932,496 B2 *  4/2011  Kato ................ H01L 31/02322
                                                 250/338.4
(Continued)

FOREIGN PATENT DOCUMENTS

JP    2002-90298 A     3/2002
JP    2010-103202 A    5/2010
(Continued)

OTHER PUBLICATIONS

Communication dated Sep. 26, 2018, issued by the European Patent Office in counterpart European Application No. 18158666.0.
(Continued)

*Primary Examiner* — Laura M Menz
(74) *Attorney, Agent, or Firm* — Sughrue Mion, PLLC

(57) ABSTRACT

An infrared detector and an infrared sensor including the infrared detector are provided. The infrared detector includes a plurality of quantum dots spaced apart from each other and including a first component, a first semiconductor layer covering the plurality of quantum dots, and a second semiconductor layer covering the first semiconductor layer.

20 Claims, 11 Drawing Sheets

(51) Int. Cl.
    H01L 31/0352    (2006.01)
    H01L 31/0224    (2006.01)
    H01L 31/109     (2006.01)
    A61B 5/00       (2006.01)
    G01N 21/3554    (2014.01)
    G01J 1/44       (2006.01)
    H01L 31/0304    (2006.01)
    G01J 5/04       (2006.01)
    B82Y 20/00      (2011.01)
    G01J 5/02       (2006.01)
    H01L 31/0384    (2006.01)
    H01L 31/101     (2006.01)
    H01L 31/105     (2006.01)
    G01J 5/08       (2006.01)

(52) U.S. Cl.
    CPC .. *H01L 31/03046* (2013.01); *H01L 31/03845* (2013.01); *H01L 31/035218* (2013.01); *H01L 31/035236* (2013.01); *H01L 31/105* (2013.01); *H01L 31/109* (2013.01); *H01L 31/1013* (2013.01); *G01J 2001/4446* (2013.01)

(56)　　　　　　　　References Cited

U.S. PATENT DOCUMENTS

| | | | | |
|---|---|---|---|---|
| 8,154,007 B2* | 4/2012 | Shieh | .............. | H01L 31/035254 257/12 |
| 8,367,452 B2* | 2/2013 | Soma | .................... | H01L 31/101 438/57 |
| 8,574,685 B1* | 11/2013 | Lewis | ................. | H01L 51/4213 427/472 |
| 8,610,232 B2* | 12/2013 | Coe-Sullivan | ...... | H01L 31/0352 257/448 |
| 8,885,135 B2* | 11/2014 | Park | .................. | G02F 1/134363 349/155 |
| 9,812,596 B2* | 11/2017 | Cho | ...................... | H01L 31/032 |
| 10,084,103 B1* | 9/2018 | Lewis | ............. | H01L 31/035218 |
| 10,304,896 B2* | 5/2019 | Park | ......................... | G01J 1/44 |
| 2009/0272903 A1* | 11/2009 | Kato | ..................... | B82Y 20/00 250/338.4 |
| 2010/0213440 A1* | 8/2010 | Shieh | ............. | H01L 31/035254 257/20 |
| 2010/0225899 A1* | 9/2010 | Treado | ............... | G01N 21/3563 356/73 |
| 2010/0326506 A1* | 12/2010 | Lifshitz | ............... | H01L 31/0352 136/255 |
| 2011/0079765 A1* | 4/2011 | Soma | .................... | H01L 31/107 257/13 |
| 2014/0061486 A1 | 3/2014 | Bao et al. | | |
| 2016/0181325 A1* | 6/2016 | Johnson | ................ | H01L 27/307 257/40 |
| 2016/0218139 A1* | 7/2016 | Ettenberg | .......... | H01L 29/66901 |
| 2016/0218233 A1* | 7/2016 | Shirane | ........... | H01L 31/035218 |
| 2016/0349573 A1* | 12/2016 | Ohmuro | .................. | G02B 5/26 |
| 2017/0084761 A1* | 3/2017 | Cho | .................. | H01L 27/14647 |
| 2017/0117308 A1* | 4/2017 | Rozploch | .............. | H01L 31/109 |
| 2019/0067362 A1* | 2/2019 | Park | .................. | H01L 31/1013 |
| 2019/0245001 A1* | 8/2019 | Park | .................. | H01L 31/03845 |

FOREIGN PATENT DOCUMENTS

| | | | |
|---|---|---|---|
| JP | 2011-171672 A | 9/2011 | |
| JP | 2016-535428 A | 11/2016 | |
| WO | WO-2006006469 A1 * | 1/2006 | ..... H01L 31/035209 |

OTHER PUBLICATIONS

European Search Report dated Jan. 14, 2019 issued in Application No. 18158666.0-1020.

Hsu, Wei-Cheng, et al, "Wavelength tuning of surface plasmon coupled quantum well infrared photodetectors", vol. 26, No. 1, Jan. 8, 2018, Optics Express, pp. 552-558.

* cited by examiner

| WAVELENGTH (nm) | BANDGAP ENERGY (eV) | IN COMP x | GA COMP. 1-x |
|---|---|---|---|
| 1650 | 0.7515 | 0.530 | 0.470 |
| 1530 | 0.8105 | 0.475 | 0.525 |
| 1450 | 0.8552 | 0.434 | 0.566 |
| 1350 | 0.9185 | 0.379 | 0.621 |

INFRARED DETECTOR AND INFRARED SENSOR INCLUDING THE SAME

CROSS-REFERENCE TO RELATED APPLICATION

This is a continuation application of U.S. patent application Ser. No. 15/870,022, filed Jan. 12, 2018, in the U.S. Patent and Trademark Office, which claims priority from Korean Patent Application No. 10-2017-0108847, filed on Aug. 28, 2017, in the Korean Intellectual Property Office, the disclosure of which is incorporated herein in its entirety by reference.

BACKGROUND

1. Field

Apparatuses consistent with exemplary embodiments relate to infrared detectors, and more particularly, to infrared detectors capable of absorbing infrared light and infrared sensors including the infrared detectors.

2. Description of the Related Art

Infrared images may be generated by detecting infrared light emitted from objects by using infrared detectors. Infrared images are typically generated by light in wavelength regions that are not identifiable by the naked human eye. However, infrared cameras perform pixel detection using infrared detectors and perform analog and digital signal processing to generate images that can be seen by the human eye. These infrared images are used in various fields such as the defense industry, medical equipment, surveillance, and security.

Infrared light is harmless to the human body and thus may be used for measuring biometric information of the human body, for example, a content of moisture and the like. However, since specific substances in the human body react only to specific frequencies of infrared light, an infrared detector uses a band pass filter to obtain information about the substance. Thus, with the inclusion of a band pass filter, it is difficult to miniaturize an infrared detector.

SUMMARY

One or more exemplary embodiments may provide infrared detectors and infrared sensors which absorb only infrared light in a specific wavelength band.

One or more exemplary embodiments may provide infrared detectors and infrared sensors which are not sensitive to temperature.

Additional exemplary aspects and advantages will be set forth in part in the description which follows and, in part, will be apparent from the description, or may be learned by practice of the presented exemplary embodiments.

According to an aspect of an exemplary embodiment, an infrared detector includes: a substrate; a first electrode, disposed on the substrate; and an infrared-absorbing layer disposed on the first electrode, wherein the infrared-absorbing layer absorbs incident infrared light in a specific wavelength band and generates a current corresponding to absorbed infrared light; and, a second electrode disposed on the infrared-absorbing layer, wherein the at least one infrared-absorbing layer includes: a first semiconductor layer including a first component; a plurality of quantum dots, spaced apart from each other on the first semiconductor layer and including a second component different from the first component; and a second semiconductor layer including the first component and the second component and covering the plurality of quantum dots.

The specific wavelength band may be determined by a content of the second component in the at least one infrared-absorbing layer.

A center wavelength of the specific wavelength band may be proportional to a content of the second component.

A center wavelength of the specific wavelength band may be 1 to 3 µm.

An energy band of the second semiconductor layer may be between an energy band of the quantum dots and an energy band of the first semiconductor layer.

The quantum dots may have a lower energy band than the first semiconductor layer and the second semiconductor layer.

The substrate may include the first component.

At least one of the first component and the second component may be a Group III element.

The first semiconductor layer may include a compound comprising the first component and a third component different from the first component and the second component, and the second semiconductor layer may include a compound comprising the first component, the second component, and the third component.

The third component may be a Group V element.

The at least one infrared-absorbing layer may include first and second infrared-absorbing layers arranged in a direction from the first electrode to the second electrode.

The infrared detector may further include at least one of: a first cladding layer between the first electrode and the infrared-absorbing layer and having an energy band higher than an energy band of the infrared-absorbing layer; and a second cladding layer between the second electrode and the infrared-absorbing layer and having an energy band higher than the energy band of the infrared-absorbing layer.

At least one of the first and second cladding layers may include a fourth component that is different from the first and second components.

The fourth component may be a metal.

The infrared detector may further include a third semiconductor layer between the at least one infrared-absorbing layer and the second electrode.

The third semiconductor layer may include a same material as the first semiconductor layer.

A sum of thicknesses of the at least one infrared-absorbing layer and the third semiconductor layer may be equal to or greater than a wavelength of the infrared light.

The sum of the thicknesses of the at least one infrared-absorbing layer and the third semiconductor layer may be a multiple of the wavelength of the infrared light.

One of the first electrode and the second electrode may include a semiconductor layer doped with n-type impurities and the other may include a semiconductor layer doped with p-type impurities.

The second electrode may include a transparent electrode.

The second electrode may overlap a portion of the infrared-absorbing layer, as viewed from an incident direction of the infrared light on the infrared detector.

According to an aspect of another exemplary embodiment, an infrared sensor includes a plurality of infrared detectors identical to the infrared detector and detecting infrared light reflected from a target object.

The plurality of infrared detectors may include a first infrared detector and a second infrared detector, arranged in a direction perpendicular to an incident direction of light.

The first infrared detector and the second infrared detector may absorb light of a same wavelength.

A substrate of the first infrared detector and a substrate of the second infrared detector may together comprise a single layer common to the first infrared detector and the second infrared detector.

A first electrode of the first infrared detector and a second electrode of the second infrared detector may be connected to each other by an electrode pad.

The plurality of infrared detectors may include a third infrared detector and a fourth infrared detector, arranged in a direction parallel to an incident direction of light.

The third infrared detector and the fourth infrared detector may absorb light having different wavelengths.

BRIEF DESCRIPTION OF THE DRAWINGS

These and/or other exemplary aspects and advantages will become apparent and more readily appreciated from the following description of the exemplary embodiments, taken in conjunction with the accompanying drawings in which.

DETAILED DESCRIPTION

Figure 1:
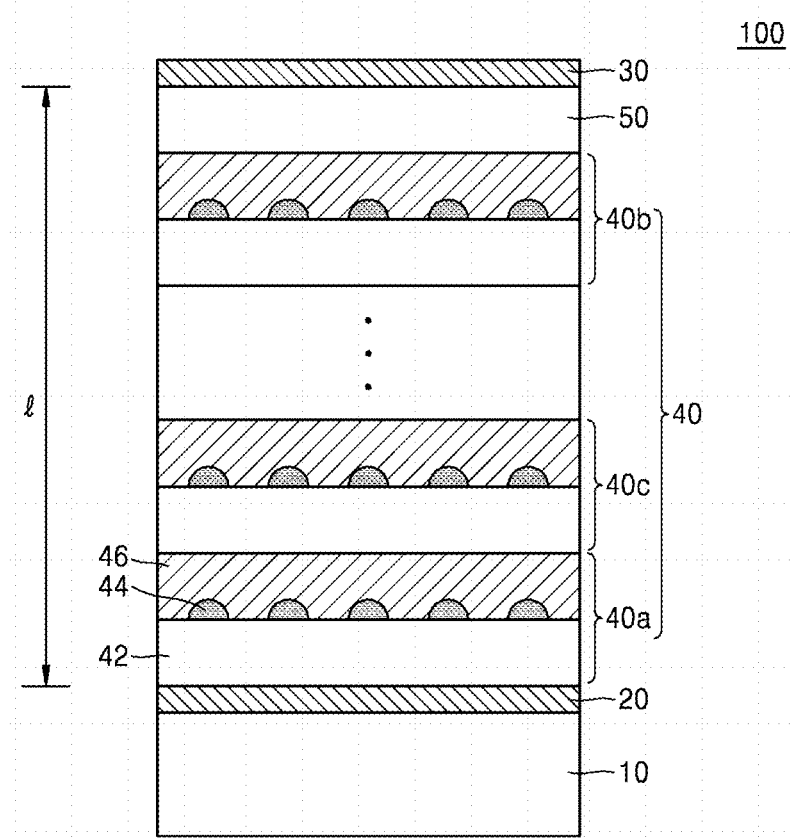
FIG. 1 is a cross-sectional view schematically illustrating an infrared detector according to an exemplary embodiment.

Infrared detectors and infrared sensors including infrared detectors will now be described in detail with reference to the accompanying drawings. In the drawings, like reference numerals refer to like elements throughout and the sizes of elements are exaggerated for clarity and convenience of explanation.

It will be understood that when an element or layer is referred to as being "on," another element or layer may include an element or a layer that is directly and indirectly on/below and left/right sides of the other element or layer. Hereafter, the inventive concept will be described more fully with reference to the accompanying drawings, in which exemplary embodiments of the inventive concept are shown.

It will be understood that, although the terms "first," "second," etc. may be used herein to describe various elements, the elements should not be limited by these terms. These terms are only used to distinguish one element from another element. Expressions such as "at least one of," when preceding a list of elements, modify the entire list of elements and do not modify the individual elements of the list.

FIG. 1 is a cross-sectional view schematically illustrating an infrared detector 100 according to an exemplary embodiment. The infrared detector 100 according to the exemplary embodiment may detect near infrared light, e.g., infrared light having a wavelength between about 750 nm and 3000 nm. As shown in FIG. 1, the infrared detector 100 may include a substrate 10, first and second electrodes 20 and 30 that are disposed on the substrate 10 and spaced apart from one another, and one or more infrared-absorbing layers 40 disposed between the first and second electrodes 20 and 30 and which absorb infrared light in a specific wavelength band to generate a current.

The infrared detector 100 may include a Group III-V semiconductor material. By forming layers of the infrared detector 100 with materials having similar lattice constants, it is easily possible to stack the layers and miniaturize the infrared detector 100.

The substrate 10 may include a Group III-V semiconductor material, and may include the same material as some layers of the infrared-absorbing layer 40 described below. For example, the substrate 10 may include GaAs.

The first and second electrodes 20 and 30 may include a conductive material, e.g., a metal material or a conductive oxide. Specifically, the first and second electrodes 20 and 30 may include a transparent conductive material. For example, the first and second electrodes 20 and 30 may include a metal oxide such as indium tin oxide (ITO) or indium zinc oxide (IZO), a metal nanoparticle dispersion thin film such as Au or Ag, a carbon nanostructure such as carbon nanotubes (CNTs) or graphene, or a conductive polymer such as poly(3,4-ethylenedioxythiophene) (PEDOT), polypyrrole (PPy), or poly(3-hexylthiophene) (P3HT).

Alternatively, the first and second electrodes 20 and 30 may include an impurity-doped semiconductor material. The first electrode 20 may be a semiconductor layer doped with impurities of a first type and may include a Group III-V semiconductor material. For example, the first electrode 20 may include GaAs doped with n-type impurities such as Si, Ge, Se, or Te. The second electrode 30 may be a semiconductor layer doped with impurities of a second type and may include a Group III-V semiconductor material. For example, the second electrode 30 may include GaAs doped with p-type impurities. As the p-type impurities, Mg, Zn, Be or the like may be used.

The infrared-absorbing layer 40 may absorb incident infrared light only within a specific wavelength band. When infrared light is incident on the infrared-absorbing layer 40, electrons, that have absorbed the energy of an energy band gap corresponding to the infrared light, move, resulting in an imbalance of electrons and holes, and a current is generated in accordance with the imbalance of electrons and holes. The current may flow from the first electrode 20 to the second electrode 30 or from the second electrode 30 to the first electrode 20 through the infrared-absorbing layer 40.

The infrared-absorbing layer 40 may also include a Group III-V semiconductor material. The infrared-absorbing layer 40 may include a first semiconductor layer 42, a plurality of quantum dots 44 that are spaced apart from each other on the first semiconductor layer 42, and a second semiconductor layer 46 covering the plurality of quantum dots 44.

The first semiconductor layer 42 may include a first component including a Group III element. For example, the first semiconductor layer 42 may include a Group III-V semiconductor material. The first semiconductor layer 42 may include a material having the highest energy band of the infrared-absorbing layer 40. For example, the first semiconductor layer 42 may include GaAs. The first semiconductor layer 42 may determine a wavelength band within which infrared light is absorbed by the infrared-absorbing layer 40.

The plurality of quantum dots 44 may be arranged on the first semiconductor layer 42. Each of the plurality of quantum dots 44 may directly contact the first semiconductor layer 42. The plurality of quantum dots 44 may be randomly arranged.

The quantum dots 44 may be nanocrystals of a semiconductor material having a diameter of about 10 nm or less. As a method of forming nanocrystals as the quantum dots 44, a vapor deposition method such as metal organic chemical vapor deposition (MOCVD) or molecular beam epitaxy (MBE), a chemical wet method in which a precursor material is added to an organic solvent to grow crystals, or the like may be used.

The quantum dots 44 may include a second component including a Group III element. For example, the quantum dots 44 may be nanocrystals of a Group III-V compound semiconductor. The Group III-V compound semiconductor nanocrystal may be any one selected from the group consisting of GaN, GaP, GaAs, AN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, and InAlPAs. When the first semiconductor layer 42 includes a GaAs material, the quantum dots 44 may include InAs having a similar lattice constant.

The nanosize quantum dots 44 exhibit a quantum confinement effect, such that a bandgap becomes larger and the bandgap has a discontinuous bandgap structure like one individual atom, unlike a bulk structure.

The quantum dots 44 are not limited to a specific structure but may have a single structure including only a core or may have any one selected from a core-single shell structure including a shell having a core and a single layer and a core-multiple shell structure including a shell having a core and multiple layers.

Figure 2:
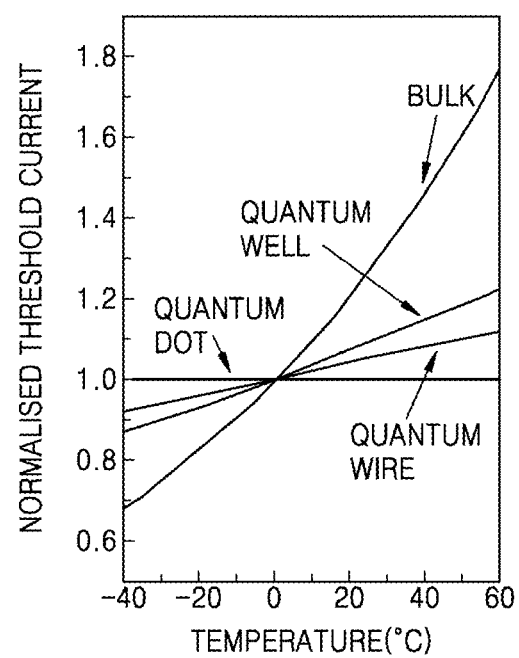
FIG. 2 is a graph showing threshold currents of various crystal structures according to temperature.

The reason why the quantum dots 44 are included in the infrared-absorbing layer 40 is that the quantum dots 44 exhibit a small change in a threshold current according to temperature. FIG. 2 is a graph showing threshold currents of various crystal structures according to temperature. As shown in FIG. 2, a bulk structure has a large change in a threshold current according to temperature. Thus, when applying a bulk structure to an infrared detector, it is necessary to keep the temperature of the infrared detector constant to improve the accuracy of the infrared detector. That is, the infrared detector may require a cooler to maintain a constant temperature. However, the quantum dots 44 do not require a cooler because the threshold current of the quantum dots 44 is almost constant according to temperature.

In addition, the quantum dots 44 may serve as seeds in depositing materials having different lattice constants to facilitate formation of layers including the materials. For example, when a layer including InGaAs, having a lattice constant different from that of GaAs, is formed on a layer including GaAs, the quantum dots 44 may serve as an adhesive.

Figure 3A:
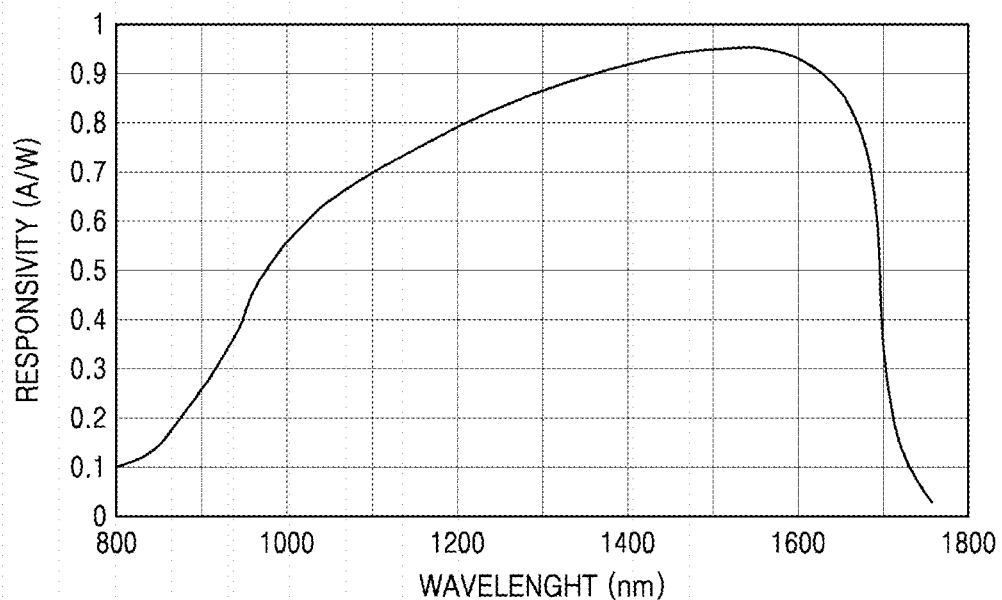
FIG. 3A is a graph showing a wavelength band within which infrared light is absorbed by a bulk structure.
Figure 3B:
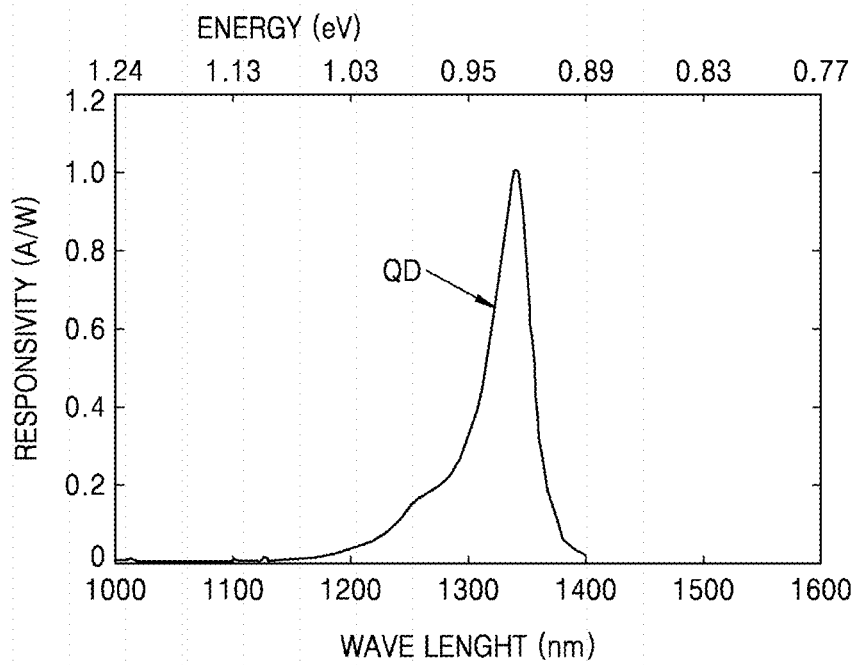
FIG. 3B is a graph showing a wavelength band within which infrared light is absorbed by quantum dots.

In addition, the quantum dots 44 may be sensitive to light in a specific wavelength band. FIG. 3A is a graph showing a wavelength band within which infrared light is absorbed by a bulk structure, and FIG. 3B is a graph showing a wavelength band within which infrared light is absorbed by quantum dots. The bulk structure used to obtain the graph of FIG. 3A includes InGaAs, and the quantum dots used to obtain the graph of FIG. 3B include InAs. As shown in FIG. 3A, the bulk structure absorbs infrared light in a wide wavelength band. The width of a wavelength band within which the responsivity of the infrared light absorbed by the bulk structure is about 0.4 or more is about 750 nm. On the other hand, as shown in FIG. 3B, the quantum dots absorb infrared light within a narrow wavelength band. The width of the wavelength band within which the responsivity of the infrared ray absorbed by the quantum dots is about 0.4 or more is about 50 nm.

An infrared detector including a bulk structure includes a bandpass filter as a component to determine whether the infrared detector absorbs infrared light in a particular wavelength band. However, an infrared detector including quantum dots has a narrow wavelength band within which infrared light is detected, and thus need not include a separate band filter. Thus, the structure of the infrared detector including the quantum dots may be simplified.

The infrared-absorbing layer 40 may include the second semiconductor layer 46 covering the plurality of quantum dots 44. The second semiconductor layer 46 may include a material having an energy band that is greater than that of the quantum dots 44. The energy band of the second semiconductor layer 46 may be greater than the energy band of the quantum dots 44 and may be less than the energy band of the first semiconductor layer 42. The second semiconductor layer 46 may include a second component contained in the quantum dots 44 and a second component including a Group III element, which is different from the second component contained in the quantum dots 44. For example, when the quantum dots 44 include InAs, the second semiconductor layer 46 may include InGaAs.

The first semiconductor layer 42, the plurality of quantum dots 44, and the second semiconductor layer 46 may include the same component. Each of the first semiconductor layer 42, the plurality of quantum dots 44, and the second semiconductor layer 46 may include a third component including a Group V element. For example, the first semiconductor layer 42 may include GaAs, the quantum dots 44 may include InAs, and the second semiconductor layer 46 may include InGaAs. By including the same material as described above, stacking between layers is facilitated.

The infrared detector 100 may further include a third semiconductor layer 50 between the infrared-absorbing layer 40 and the second electrode 30. The third semiconductor layer 50 may include the same material as the first semiconductor layer 42. For example, the third semiconductor layer 50 may also include GaAs.

The upper surface of the infrared-absorbing layer 40 may be planarized so that a plurality of infrared-absorbing layers may be stacked. The quantum dots 44 have a crystal structure, and the second semiconductor layer 46 may have the form of a thin film and may cover the quantum dots 44. Thus, the surface of the second semiconductor layer 46 may be curved by the quantum dots 44, and the infrared-absorbing layer 40 may be planarized by the stacking of the first semiconductor layer 42.

The infrared detector 100 may include one or more infrared-absorbing layers 40. When the infrared detector 100 includes one or more infrared-absorbing layers 40, the one or more infrared-absorbing layers 40 may be arranged in a direction from the first electrode 20 to the second electrode 30. For example, the one or more infrared-absorbing layers 40 may include a first infrared-absorbing layer 40a, disposed on and in contact with the first electrode 20, a second infrared-absorbing layer 40b, disposed below and in contact with the third semiconductor layer 50, and a third infrared-absorbing layer 40c arranged between the first infrared-absorbing layer 40a and the second infrared-absorbing layer 40b.

The one or more infrared-absorbing layers 40 and the third semiconductor layer 50 may determine the content of In component contained in the infrared-absorbing layers 40. Since the In component is contained in the quantum dots 44 and the second semiconductor layer 46, the content of the In component may be adjusted by adjusting the thicknesses of the first semiconductor layer 42 and the third semiconductor layer 50. For example, since the content of the Ga component increases as the thicknesses of the first semiconductor layer 42 and of the third semiconductor layer 50 increase, the content of the In component may be comparatively reduced. In the infrared detector 100 according to the present exemplary embodiment, the content of the In component may be determined so that infrared light having a center wavelength of about 1 to 3 μm is absorbed.

The sum (t) of the thicknesses of the one or more infrared-absorbing layers 40 and the third semiconductor layer 50 may be greater than or equal to the wavelength of the infrared light to be detected. For example, the sum of the thicknesses of the one or more infrared-absorbing layers 40 and the third semiconductor layer 50 may be a multiple of the wavelength of the infrared light to be detected. Thus, the infrared light to be detected may be stably incident on the infrared-absorbing layer 40.

Figures 4, 5:
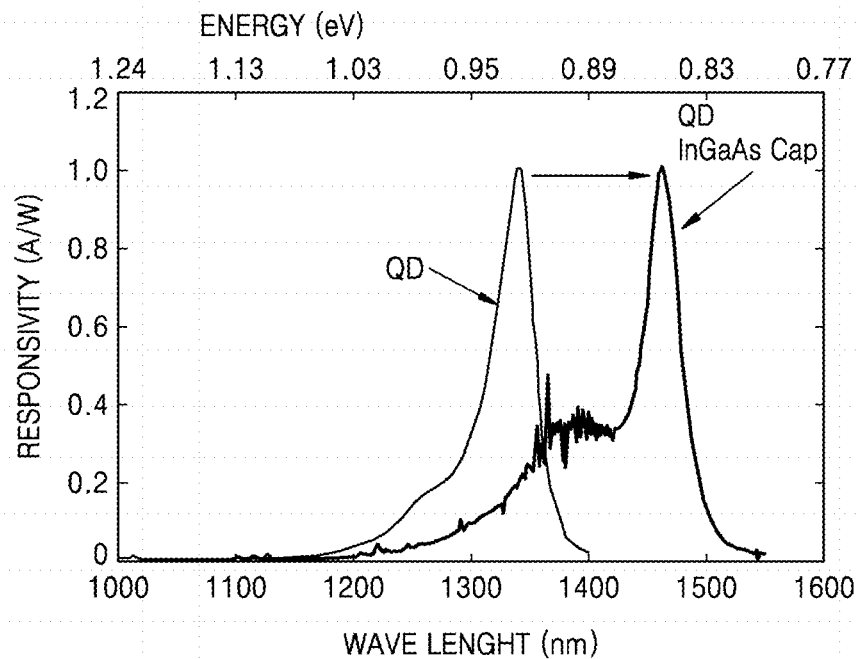
FIG. 4 is a graph showing the wavelength of infrared light absorbed by quantum dots according to an exemplary embodiment and the wavelength of infrared light absorbed by quantum dots doped with the material of a first semiconductor layer.
FIG. 5 is a table showing a relationship between a center wavelength and the content of indium (In), according to an exemplary embodiment.

FIG. 4 is a graph showing the wavelength of infrared light absorbed by quantum dots according to an exemplary embodiment and the wavelength of infrared light absorbed by quantum dots doped with a second semiconductor layer. As shown in FIG. 4, it may be seen that quantum dots (i.e., the quantum dots 44), including InAs, react to infrared light having a center wavelength of about 1350 nm, whereas quantum dots doped with InGaAs react to infrared light having a center wavelength of about 1460 nm. That is, it may be seen that the degree of doping of InGaAs may change the wavelength band of infrared light to which quantum dots react.

Also, it may be seen from FIG. 4 that even if the wavelength band of infrared light to which quantum dots react is changed, the width of the wavelength band of the infrared light to which quantum dots react is almost constant. For example, quantum dots including InAs and a responsivity of quantum dots doped with InGaAs may be 0.4 or more at the width of the wavelength band of about 50 nm. Thus, the detection sensitivity of infrared light may be maintained while adjusting a wavelength band to be detected by the doping of InGaAs.

The band gap energy Eg(x) of $In_xGa_{1-x}As$ is expressed by Equation (1).

$$Eg(x) = 1.425 \text{ eV} - 1.501x \text{ eV} + 0.436x^2 \text{ eV}$$ [Equation 1]

Here, x is equal to or greater than 0 and is equal to or less than 10 (i.e., 0≤x≤10).

As shown in Equation 1, the band gap energy Eg(x) changes depending on the content of In component. A change in the bandgap energy Eg(x) means that the wavelength of infrared light to be absorbed may be changed.

FIG. 5 is a table showing a relationship between a center wavelength and the content of In component, according to an exemplary embodiment. As shown in FIG. 5, it may be seen that the content of In component and a band gap energy are proportional to each other and the content of In component and the center wavelength of infrared light to be absorbed are inversely proportional to each other. Thus, the center wavelength of infrared light to be absorbed may be adjusted by controlling the content of In component.

Figure 6:
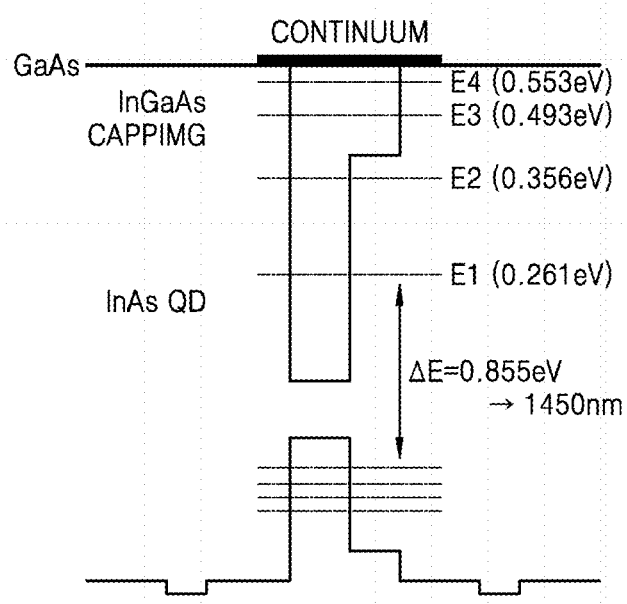
FIG. 6 is a diagram illustrating an energy band of an infrared-absorbing layer in an infrared detector according to an exemplary embodiment.

FIG. 6 is a diagram illustrating an energy band of the infrared-absorbing layer 40 in the infrared detector 100 according to the exemplary embodiment. When the first semiconductor layer 42 includes GaAs, the quantum dots 44 include InAs, and the second semiconductor layer 46 includes InGaAs, the infrared-absorbing layer 40 may have an energy band as shown in FIG. 6. When electrons of the infrared-absorbing layer 40 absorb infrared light having a specific wavelength, for example, the wavelength of 1450 nm, the electrons are activated and move.

Figure 7:
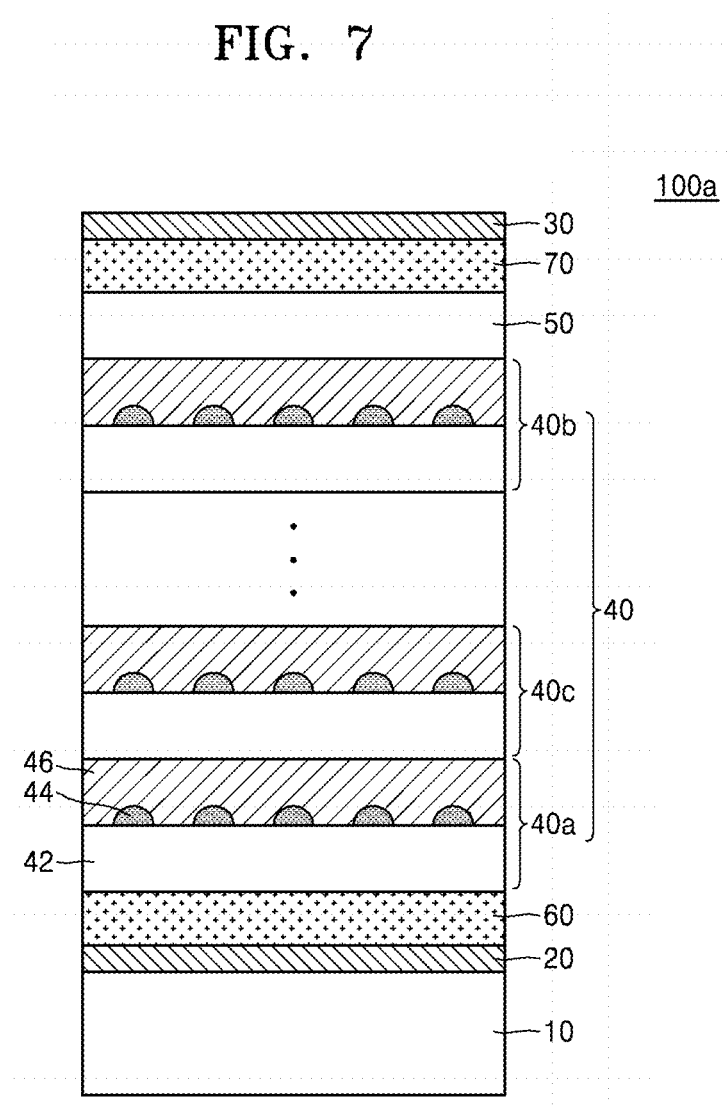
FIG. 7 is a cross-sectional view illustrating an infrared detector according to another exemplary embodiment.

FIG. 7 is a cross-sectional view illustrating an infrared detector 100a according to another exemplary embodiment. When comparing FIG. 7 with FIG. 1, the infrared detector 100a of FIG. 7 may further include a first cladding layer 60 arranged between a first electrode 20 and an infrared-absorbing layer 40 and a second cladding layer 70 arranged between a second electrode 30 and the infrared-absorbing layer 40. The first cladding layer 60 and the second cladding layer 70 may include a material having an energy band higher than the energy band of the infrared-absorbing layer 40. The first cladding layer 60 and the second cladding layer 70 may include a metal material. For example, the first cladding layer 60 and the second cladding layer 70 may include AlGaAs. Even if electrons of the infrared-absorbing layer 40 are activated, the first cladding layer 60 and the second cladding layer 70 may allow only electrons having a higher energy band than the first cladding layer 60 and the second cladding layer 70 to escape from the infrared-absorbing layer 40, thereby increasing the electron concentration of the infrared-absorbing layer 40. The infrared detector 100a may include both the first cladding layer 60 and the second cladding layer 70 or may include only one of the first cladding layer 60 and the second cladding layer 70.

Figure 8:
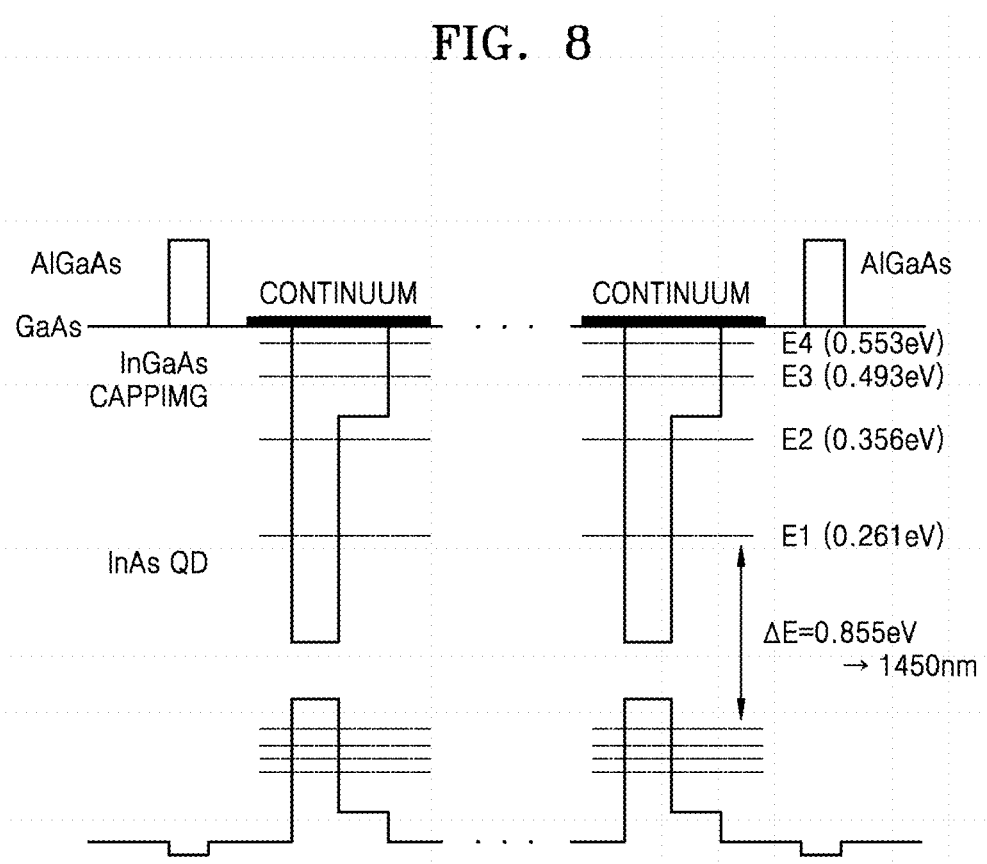
FIG. 8 is a diagram illustrating energy bands of an infrared-absorbing layer and cladding layers of FIG. 7.

FIG. 8 is a diagram illustrating energy bands of the infrared-absorbing layer 40 and the first and second cladding layers 60 and 70 of FIG. 7. When the first and second cladding layers 60 and 70 include AlGaAs, the quantum dots 44 include InAs, and the second semiconductor layer 46 includes InGaAs, the infrared-absorbing layer 40 and the first and second cladding layers 60 and 70 may have energy bands as shown in FIG. 8. Since a band gap up to a first energy band is 0.855 eV, electrons may be activated when infrared light of about 1450 nm is incident on the infrared-absorbing layer 40. However, only electrons having a higher energy band than the first and second cladding layers 60 and 70 may escape from the infrared-absorbing layer 40 and flow to the first electrode 20 or the second electrode 30.

An infrared sensor may be formed by arranging a plurality of infrared detectors, for example, the infrared detectors 100 or 100a described above. The plurality of infrared detectors of the infrared sensor may detect infrared light of the same wavelength band or detect infrared light of different wavelength bands. The wavelength band of infrared light to be detected may vary depending on the content of In in the an infrared-absorbing layer included in each of the infrared detectors 100 or 100*a*.

Figure 9:
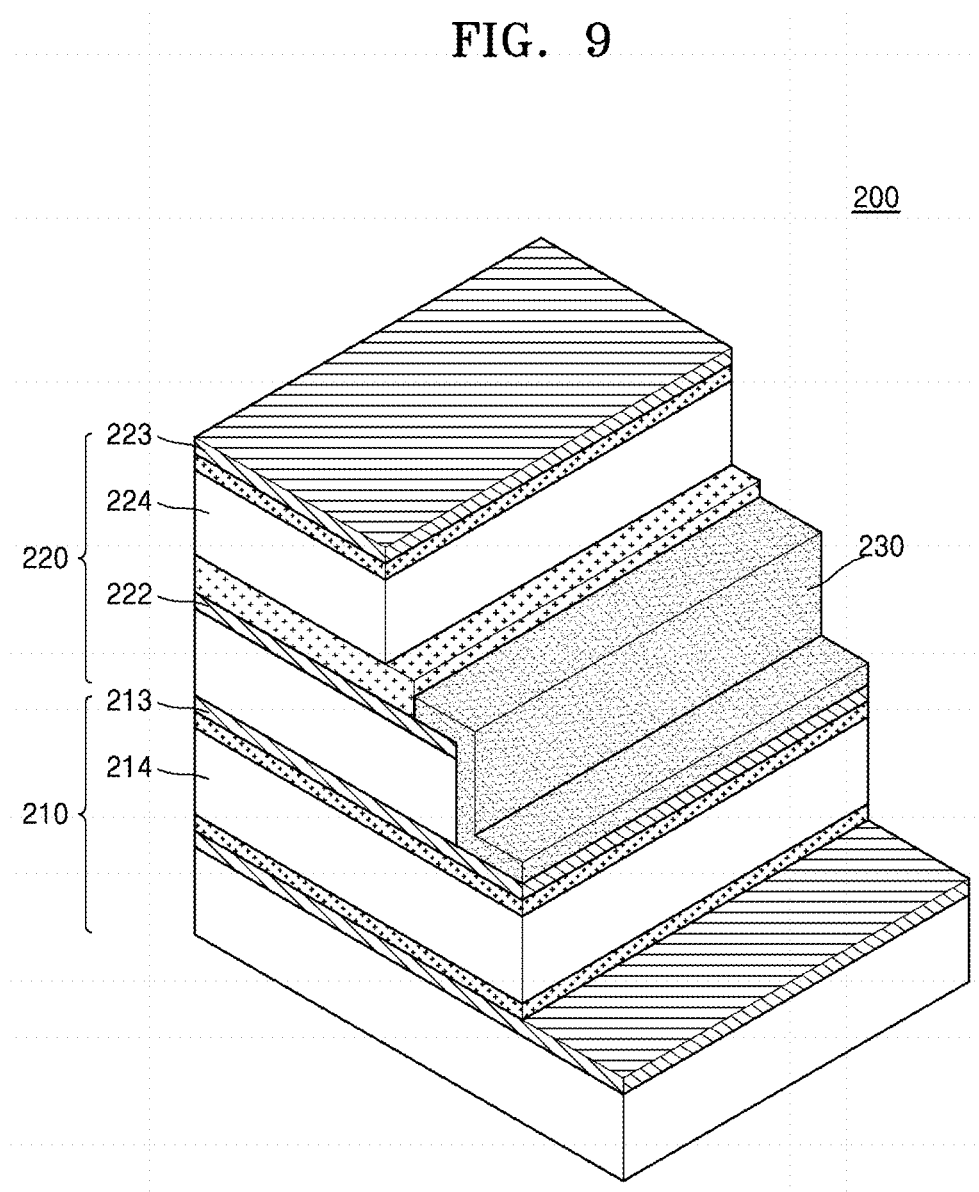
FIG. 9 is a view illustrating an infrared sensor according to an exemplary embodiment.

FIG. 9 is a view illustrating an infrared sensor 200 according to an exemplary embodiment. As shown in FIG. 9, the infrared sensor 200 may include a plurality of infrared detectors, for example, first and second infrared detectors 210 and 220. For example, the first and second infrared detectors 210 and 220 may be stacked in a direction parallel to an incident direction of infrared light. Each of the first and second infrared detectors 210 and 220 may correspond to the infrared detector 100 shown in FIG. 1 or the infrared detector 100*a* shown in FIG. 8.

A second electrode 213 of the first infrared detector 210 and a first electrode 222 of the second infrared detector 220 may be connected to each other by an electrode contact 230. The second electrode 213 of the first infrared detector 210 and the first electrode 222 of the second infrared detector 220 may be a single electrode common to both the first infrared detector 210 and the second infrared detector 220. The second electrode 213 of the first infrared detector 210, the first electrode 222 of the second infrared detector 220, and a second electrode 223 of the second infrared detector 220 may be transparent electrodes in order to increase an incident amount of infrared light.

The content of In may be different between an infrared-absorbing layer 214 of the first infrared detector 210 and an infrared-absorbing layer 224 of the second infrared detector 220. Thus, the first infrared detector 210 and the second infrared detector 220 may detect different wavelength bands. The longer the wavelength, the higher the transmittance, and thus, the first infrared detector 210 may be designed to detect a longer wavelength than the second infrared detector 220. For example, the content of In may be adjusted so that the first infrared detector 210 detects infrared light having a center wavelength of about 1650 nm and the second infrared detector 220 detects infrared light having a center wavelength of about 1450 nm.

Figure 10:
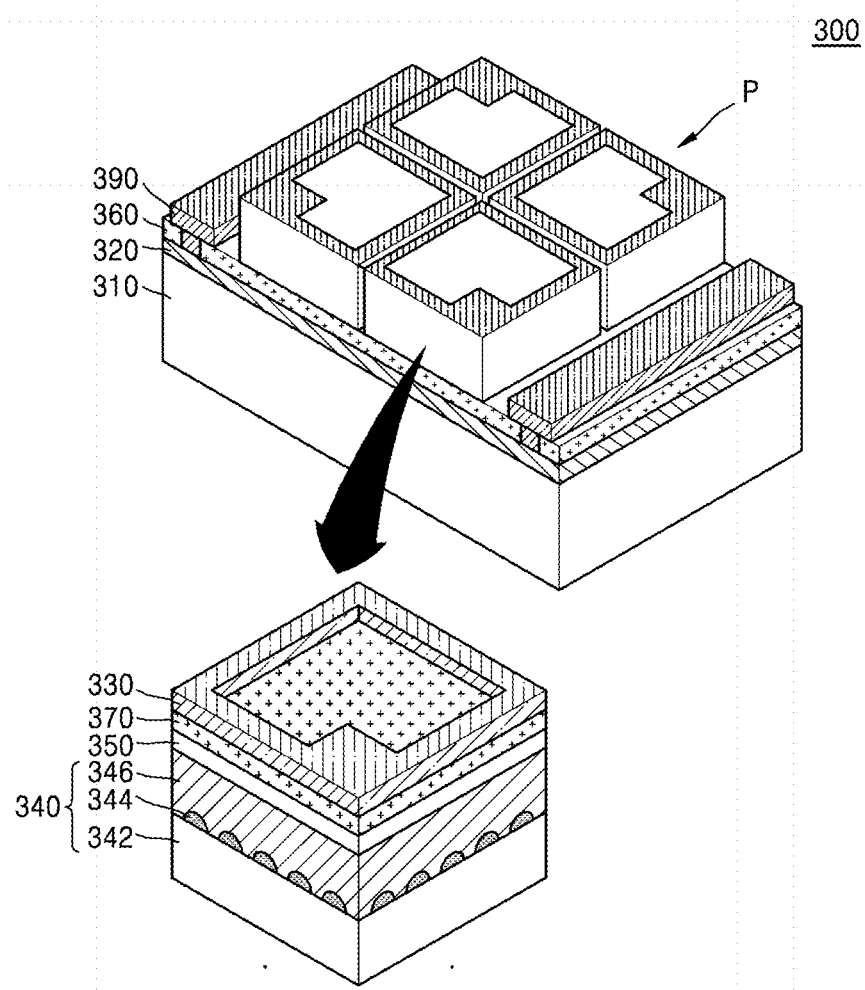
FIG. 10 is a view illustrating an infrared sensor according to another exemplary embodiment.

FIG. 10 is a view illustrating an infrared sensor 300 according to another exemplary embodiment. As shown in FIG. 10, the infrared sensor 300 may include a plurality of pixels P arranged on a substrate 310. The plurality of pixels P may be arranged in a direction perpendicular to an incident direction of infrared light. Since the plurality of pixels P are arranged in the direction perpendicular to the incident direction of infrared light, an object having a certain area may be photographed at once. The pixels P may be formed by the infrared detector 100.

The substrate 310 of the infrared sensor 300 may include a Group III-V semiconductor material. For example, the substrate 310 may include GaAs.

A common electrode 320 may be arranged on the substrate 310. The common electrode 320 may include a metal material or a conductive oxide. Alternatively, the common electrode 320 may include a semiconductor material doped with impurities. For example, the common electrode 320 may include GaAs doped with n-type impurities.

A first cladding layer 360 may be arranged on the common electrode 320, and the first cladding layer 360 may include a material having an energy band higher than that of an infrared-absorbing layer 340 included in each of the pixels P. For example, the first cladding layer 360 may include AlGaAs. An electrode pad 390 may be arranged on a portion of the first cladding layer 360. The electrode pad 390 may be connected to the common electrode 320 through a through-hole of the first cladding layer 360.

Each pixel P may include one or more infrared-absorbing layers 340, a third semiconductor layer 350, a second cladding layer 370, and a pixel electrode 330. The infrared-absorbing layers 340, the third semiconductor layer 350, and the second cladding layer 370, included in the pixel P, may respectively correspond to the infrared-absorbing layer 40, the third semiconductor layer 50, and the second cladding layer 70, shown in FIG. 7.

Specifically, each of the infrared-absorbing layers 340 may include a Group III-V semiconductor material. Each of the infrared-absorbing layers 340 may include a first semiconductor layer 342, a plurality of quantum dots 344 that are spaced apart from one another on the first semiconductor layer 342, and a second semiconductor layer 346 covering the plurality of quantum dots 344.

The first semiconductor layer 342 may also include a Group III-V semiconductor material. The first semiconductor layer 342 may include a material having the highest energy band of all of the layers in the infrared-absorbing layer 340. The first semiconductor layer 342 may also include a first component including a Group III element. For example, the first semiconductor layer 342 may include GaAs.

The plurality of quantum dots 344 may be randomly arranged. The quantum dots 344 may include a second component including a Group III element. Specifically, the quantum dots 344 may be nanocrystals of a Group III-V-based compound semiconductor. For example, the quantum dots 344 may include InAs.

The second semiconductor layer 346 covering the plurality of quantum dots 344 may include a material having an energy band higher than that of the quantum dots 344. The second semiconductor layer 346 may include a component including a Group III element, which is not included in the quantum dots 344. For example, when the quantum dots 344 include InAs, the second semiconductor layer 346 may include InGaAs.

The third semiconductor layer 350 may be arranged on the infrared-absorbing layer 340 and may include a Group III-V semiconductor material. For example, the third semiconductor layer 350 may include GaAs.

The second cladding layer 370 may be arranged on the third semiconductor layer 350 and may include a material having an energy band higher than that of the infrared-absorbing layer 340. The second cladding layer 370 may include AlGaAs, like the first cladding layer 360.

The pixel electrode 330 may include a conductive material and may correspond to the second electrode 30 of the infrared detector 100 shown in FIG. 1 or of the infrared detector 100*a* shown in FIG. 7. For example, the pixel electrode 330 may include a metal material or a conductive oxide. Specifically, the pixel electrode 330 may include a transparent conductive material. For example, the pixel electrode 330 may include a metal oxide such as ITO or IZO, a metal nanoparticle dispersion thin film such as Au or Ag, a carbon nanostructure such as CNT or graphene, or a conductive polymer such as PEDOT, PPy, or P3HT.

Alternatively, the pixel electrode 330 may include a semiconductor material doped with impurities. For example, the pixel electrode 330 may include a semiconductor material of GaAs doped with p-type impurities.

When the material of the pixel electrode 330 is not a transparent material, the pixel electrode 330 may have a shape having an empty center region, in order to increase the incident amount of infrared light. For example, the pixel electrode 330 may have the shape of a ring arranged only on the edges of the infrared-absorbing layer 340. Alternatively, an electrode of the pixel P may have the shape of a mesh including a plurality of openings.

The pixel P, the first cladding layer 360, the common electrode 320, and a part of the substrate 310, shown in FIG. 10, may correspond to the infrared detector 100a shown in FIG. 7. The infrared sensor 300 of FIG. 10 includes the first and second cladding layers 360 and 370, but is not limited thereto. For example, the infrared sensor 300 may omit the first and second cladding layers 360 and 370, or may include only one of the first and second cladding layers 360 and 370.

Figure 11:
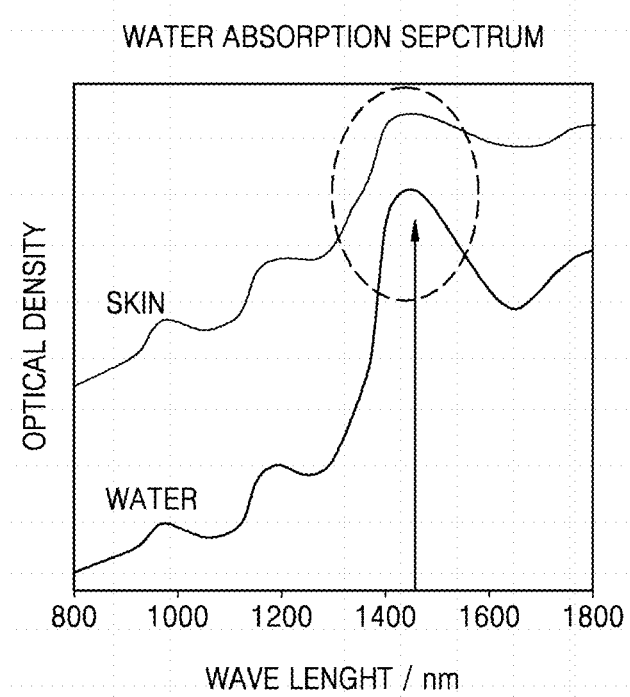
FIG. 11 is a graph showing light absorption rates according to materials.

The infrared sensor 300 described above may be used to measure the content of a component contained in an object. For example, the infrared sensor 300 may be used as a sensor for measuring moisture. FIG. 11 is a graph showing light absorption rates according to materials. As shown in FIG. 11, it may be seen that water absorbs more infrared light in a wavelength band of about 1450 nm. Skin includes various materials, but the content of water in the skin is relatively high, and thus, as shown in FIG. 11, it may be seen that the skin has a light absorption rate similar to the light absorption rate of water. Particularly, it may be seen that the skin also absorbs infrared light in a wavelength band of about 1450 nm. Thus, the moisture of the skin may be measured by using infrared light in a wavelength band of about 1450 nm.

An infrared sensor 300 according to the present exemplary embodiment may be designed to detect infrared light in a wavelength band of about 1450 nm in order to measure a moisture content. The In content of an infrared-absorbing layer in the infrared sensor 300 may be determined to detect infrared light in a wavelength band of about 1450 nm. For example, the infrared sensor 300 may be manufactured to have an In content of about 0.43. The infrared sensor 300 may also be used to measure other components in addition to moisture.

Figure 12A:
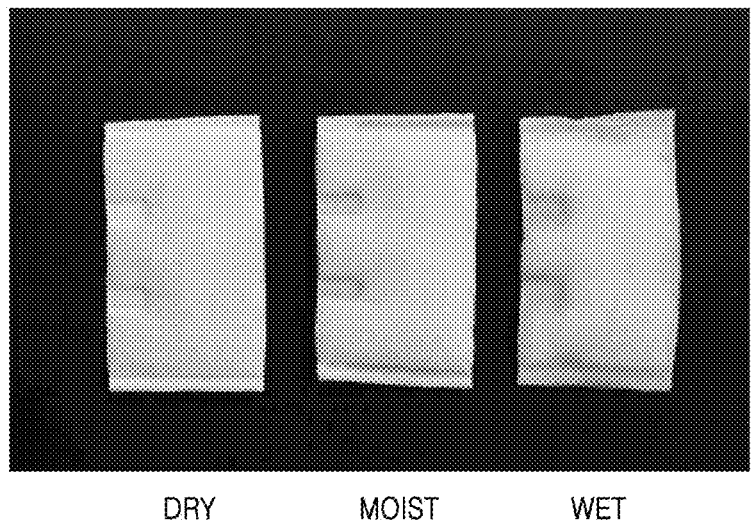
FIG. 12A shows a result obtained by photographing a plurality of sheets having different moisture content ratios with a general camera.
Figure 12B:
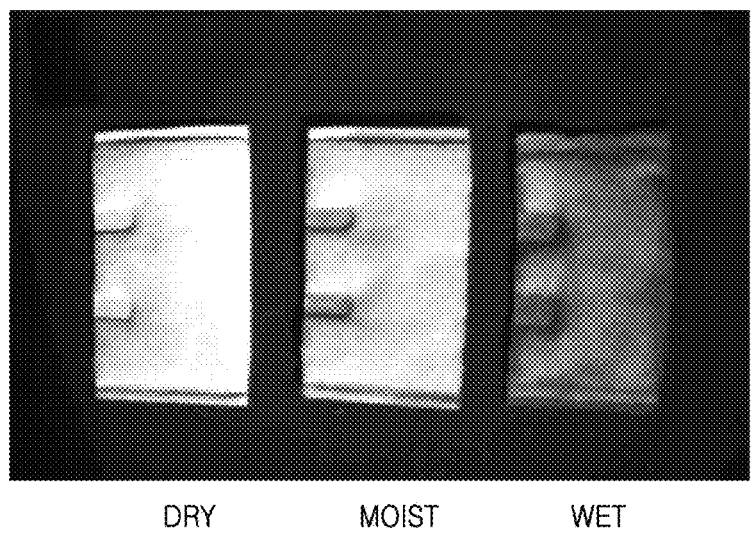
FIG. 12B shows a result obtained by photographing a plurality of sheets having different moisture content ratios with an infrared sensor.

FIG. 12A shows a result obtained by photographing a plurality of sheets having different moisture content ratios with a general camera, and FIG. 12B shows a result obtained by photographing a plurality of sheets having different moisture content ratios with an infrared sensor. As shown in FIG. 12A, since the general camera is an RGB image device, the general camera does not provide information about the content of moisture in the sheets. On the other hand, as shown in FIG. 12B, the infrared sensor may provide a lower luminance image with respect to a sheet having a higher moisture content ratio. A sheet having a higher moisture content ratio may absorb more infrared light in a wavelength band of about 1450 nm. Thus, in this case, since the infrared sensor absorbs less infrared light, the infrared sensor generates lower current and provides a lower luminance image.

As described above, when quantum dots are included in an infrared detector and an infrared sensor, the infrared detector and the infrared sensor may detect infrared light within a narrow bandwidth. Thus, the infrared detector and the infrared sensor do not require a separate band-pass filter. In addition, since the threshold current in the quantum dots does not change significantly according to temperature, the infrared detector and the infrared sensor do not require a cooler for maintaining a constant temperature. Thus, a small infrared detector and a small infrared sensor may be manufactured.

In addition, since the infrared detector having a multilayer structure includes quantum dots having an adhesive function, multiple layers in the infrared detector may be easily formed and thus the manufacture of the infrared detector is facilitated.

It should be understood that exemplary embodiments described herein should be considered in a descriptive sense only and not for purposes of limitation. Descriptions of features or aspects within each embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An infrared detector comprising:
a substrate;
a first electrode, disposed on the substrate; and
an infrared-absorbing layer disposed on the first electrode, comprising a plurality of quantum dots configured to absorb infrared light having a width of wavelength band of about 50 nm or less within which a responsivity of the infrared light absorbed by the plurality of quantum dots is about 0.4 or more and generate a current corresponding to absorbed infrared light; and
a second electrode disposed on the infrared-absorbing layer,
wherein the first electrode, the infrared-absorbing layer, and the second electrode are sequentially arranged from the substrate, and the current generated in the infrared-absorbing flows in a direction perpendicular to the substrate.

2. The infrared detector of claim 1, wherein the infrared light comprises a wavelength band absorbed by moisture.

3. The infrared detector of claim 1, wherein the infrared light is received from a target object and the infrared-absorbing layer generates a current having a magnitude in inverse proportion to a content of moisture in the target object.

4. The infrared detector of claim 1, wherein a center wavelength is about 1450 nm.

5. The infrared detector of claim 1, wherein the infrared-absorbing layer comprises a first infrared-absorbing layer and a second infrared-absorbing layer arranged in a direction from the first electrode to the second electrode.

6. The infrared detector of claim 1, wherein one of the first electrode and the second electrode comprises a semiconductor layer doped with n-type impurities and another one of the first electrode and the second electrode comprises a semiconductor layer doped with p-type impurities.

7. The infrared detector of claim 1, wherein the infrared-absorbing layer comprises at least one of a first semiconductor layer comprising a first component and a second semiconductor layer comprising the first component and a second component, different from the first component.

8. The infrared detector of claim 7, wherein the plurality of quantum dots comprising the second component.

9. The infrared detector of claim 7, wherein the second semiconductor layer covers the plurality of quantum dots.

10. The infrared detector of claim 7, wherein a wavelength band of the absorbed infrared light is determined by a content of the second component in the infrared-absorbing layer.

11. The infrared detector of claim 7, wherein the second component comprises In.

12. The infrared detector of claim 7, wherein an energy band of the second semiconductor layer is between an energy band of the plurality of quantum dots and an energy band of the first semiconductor layer.

13. The infrared detector of claim 7, wherein an energy band of the plurality of quantum dots is lower than an energy band of the first semiconductor layer and lower than an energy band of the second semiconductor layer.

14. The infrared detector of claim 7, wherein the substrate comprises the first a component.

15. The infrared detector of claim 7, wherein at least one of the first component and the second component is a Group III element.

16. The infrared detector of claim 7, wherein the first semiconductor layer comprises a first compound comprising the first component and a third component, different from the first component and the second component, and the second semiconductor layer comprises a second compound comprising the first component, the second component, and the third component.

17. An infrared sensor comprising a plurality of infrared detectors, each identical to the infrared detector according to claim 1, wherein the infrared sensor is configured to detect the infrared light received from a target object.

18. The infrared sensor of claim 17, wherein the plurality of infrared detectors comprise a first infrared detector and a second infrared detector, arranged in a direction perpendicular to a direction of incidence of the infrared light on the infrared sensor.

19. The infrared sensor of claim 17, wherein the plurality of infrared detectors comprise a third infrared detector and a fourth infrared detector, arranged in a direction of incidence of the infrared light on the infrared sensor.

20. An infrared detector comprising:
a substrate;
a first electrode, disposed on the substrate; and
an infrared-absorbing layer disposed on the first electrode, comprising a plurality of quantum dots configured to absorb infrared light having a width of wavelength band of about 50 nm or less within which a responsivity of the infrared light absorbed by the plurality of quantum dots is about 0.4 or more and generate a current corresponding to absorbed infrared light; and
a second electrode disposed on the infrared-absorbing layer,
wherein one of the first electrode and the second electrode comprises a semiconductor layer doped with n-type impurities and another one of the first electrode and the second electrode comprises a semiconductor layer doped with p-type impurities.

* * * * *